(12) United States Patent
Nessel

(10) Patent No.: US 9,770,562 B2
(45) Date of Patent: Sep. 26, 2017

(54) LOCK OUT MEMBER WITH DIFFERENT CROSS SECTIONS

(75) Inventor: Christiane Nessel, Frankurt am Main (DE)

(73) Assignee: SANOFI-AVENTIS DEUTSCHLAND GMBH, Frankfurt am Main (DE)

(*) Notice: Subject to any disclaimer, the term of this patent is extended or adjusted under 35 U.S.C. 154(b) by 0 days.

(21) Appl. No.: 14/113,861

(22) PCT Filed: May 4, 2012

(86) PCT No.: PCT/EP2012/058258
§ 371 (c)(1),
(2), (4) Date: Oct. 25, 2013

(87) PCT Pub. No.: WO2012/152697
PCT Pub. Date: Nov. 15, 2012

(65) Prior Publication Data
US 2014/0081212 A1  Mar. 20, 2014

(30) Foreign Application Priority Data
May 6, 2011 (EP) .................................. 11165120

(51) Int. Cl.
*A61M 5/32* (2006.01)
*A61M 5/50* (2006.01)
(Continued)

(52) U.S. Cl.
CPC ............... *A61M 5/50* (2013.01); *A61M 5/19* (2013.01); *A61M 5/20* (2013.01); *A61M 5/2066* (2013.01);
(Continued)

(58) Field of Classification Search
CPC .......... A61M 5/31535; A61M 5/31536; A61M 5/31538; A61M 2005/3154;
(Continued)

(56) References Cited

U.S. PATENT DOCUMENTS 5,314,412 A    5/1994  Rex
5,658,257 A *  8/1997  Ryles .................. A61M 5/3234
                                                           604/110
(Continued)

FOREIGN PATENT DOCUMENTS

CN    101641127    2/2010
CN      1817379 B   6/2010
(Continued)

OTHER PUBLICATIONS

International Search Report for Int. App. No. PCT/EP2012/058258, completed Aug. 13, 2012.

*Primary Examiner* — Bhisma Mehta
*Assistant Examiner* — William Frehe
(74) *Attorney, Agent, or Firm* — McDonnell Boehnen Hulbert & Berghoff LLP

(57) ABSTRACT

An apparatus is presented comprising a lock out member configured to be implemented into a medical device, in particular a dispense interface, attachable to a second medical device, in particular a main body, wherein said lock out member is configured to prevent a second attachment of said medical device to said second medical device, wherein said lock out member has at least a first area with a first cross-sectional area, wherein said lock out member has at least a second area having a second cross-sectional area smaller than the first cross-sectional area, such that an electric resistance is defined between opposite ends of the lockout member and wherein said lock out member, at least in the second area, is made of a conductive material.

15 Claims, 14 Drawing Sheets

(51) Int. Cl.
  *G01R 27/02* (2006.01)
  *A61M 5/19* (2006.01)
  *A61M 5/20* (2006.01)

(52) U.S. Cl.
  CPC ........... *A61M 5/3294* (2013.01); *G01R 27/02* (2013.01); *A61M 5/5086* (2013.01); *A61M 2205/27* (2013.01)

(58) Field of Classification Search
  CPC .... A61M 5/31541; A61M 5/50; A61M 5/504; A61M 39/16; A61M 2039/1022; A61M 5/3294; A61M 5/5086; A61M 5/20; A61M 5/2066; A61M 5/19; G01R 27/02
  USPC .................................................. 604/110, 111
  See application file for complete search history.

(56) References Cited

U.S. PATENT DOCUMENTS

| | | | |
|---|---|---|---|
| 6,749,588 B1 * | 6/2004 | Howell | A61M 5/3273 604/110 |
| 7,207,969 B2 * | 4/2007 | Epstein et al. | 604/82 |
| 2003/0139774 A1 | 7/2003 | Epstein et al. | |
| 2007/0038187 A1 * | 2/2007 | Albert | A61M 5/3273 604/164.08 |
| 2008/0065083 A1 * | 3/2008 | Truckai | A61B 17/3472 600/407 |
| 2008/0154192 A1 * | 6/2008 | Schraga | A61M 5/50 604/110 |
| 2012/0150125 A1 * | 6/2012 | Karlsson | A61M 5/326 604/198 |

FOREIGN PATENT DOCUMENTS

| | | |
|---|---|---|
| EP | 0710487 | 5/1996 |
| JP | H10-511014 | 10/1998 |
| JP | 2002-518108 | 6/2002 |
| JP | 2010-535040 | 11/2010 |
| WO | 94/11039 | 5/1994 |
| WO | 02/45786 A2 | 6/2002 |
| WO | 2008/113772 | 9/2008 |
| WO | 2008/140546 | 11/2008 |

* cited by examiner

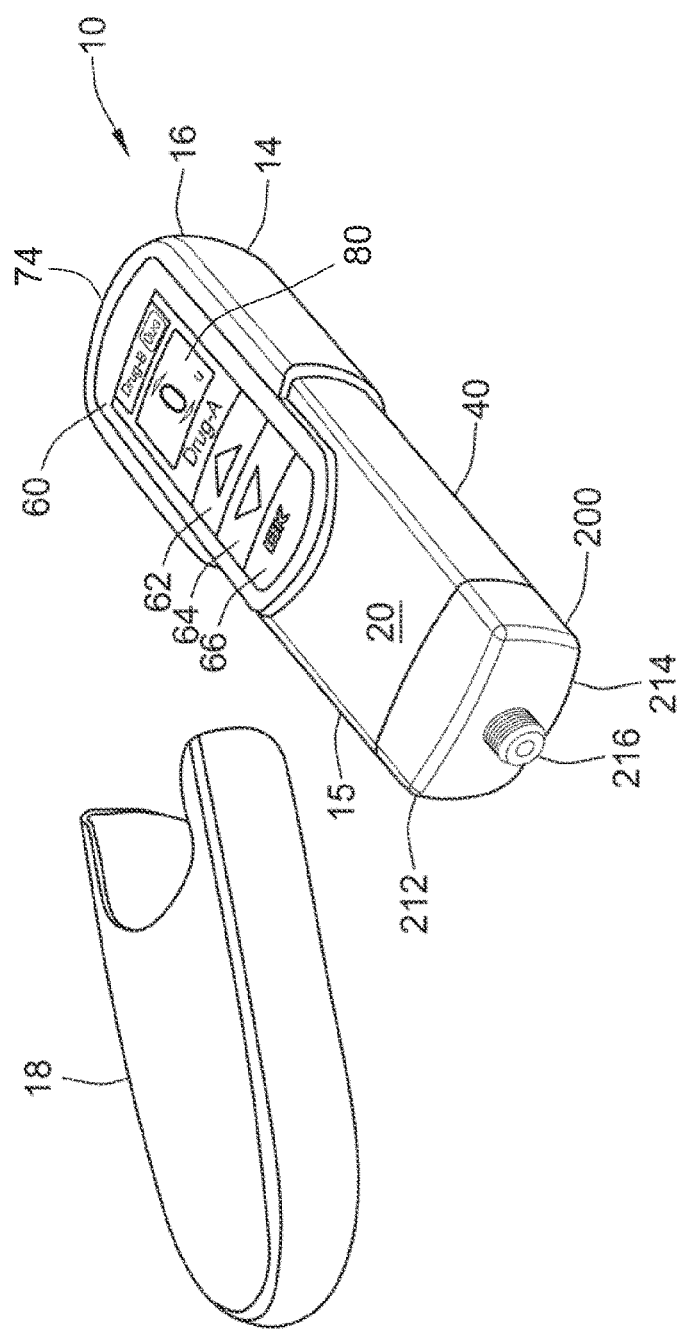

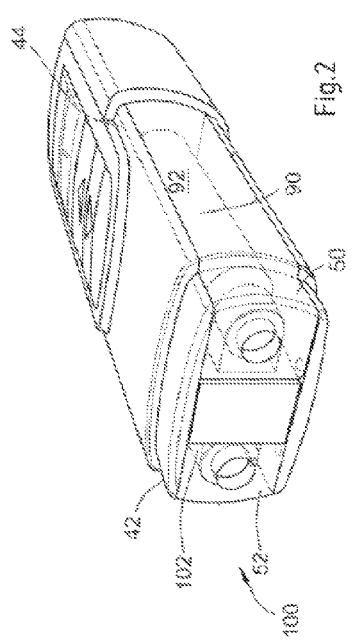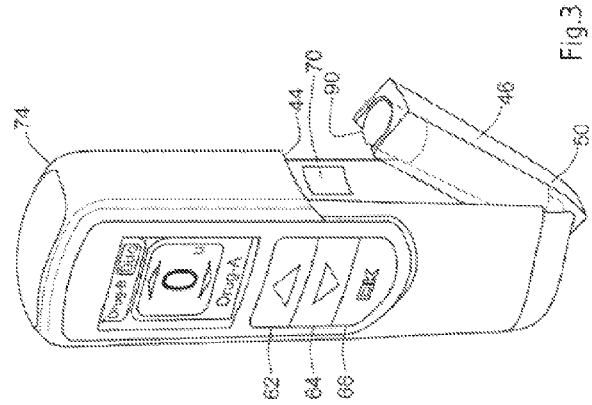

LOCK OUT MEMBER WITH DIFFERENT CROSS SECTIONS

CROSS REFERENCE TO RELATED APPLICATIONS

The present application is a U.S. National Phase Application pursuant to 35 U.S.C. §371 of International Application No. PCT/EP2012/058258 filed May 4, 2012, which claims priority to European Patent Application No. 11165120.4 filed May 6, 2011. The entire disclosure contents of these applications are herewith incorporated by reference into the present application.

FIELD OF DISCLOSURE

The present patent application relates to medical devices of delivering at least two drug agents from separate reservoirs. Such drug agents may comprise a first and a second medicament. The medical device includes a dose setting mechanism for delivering the drug automatically or manually by the user.

The drug agents may be contained in two or more multiple dose reservoirs, containers or packages, each containing independent (single drug compound) or pre-mixed (co-formulated multiple drug compounds) drug agents.

BACKGROUND

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then only combined and/or delivered to the patient during a single delivery procedure. These active agents may be administered together in a combined dose or alternatively, these active agents may be combined in a sequential manner, one after the other.

SUMMARY

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with the primary reservoir and with a secondary reservoir of medicament containing at least one drug agent. The drug dispense interface can be a type of outlet that allows the two or more medicaments to exit the system and be delivered to the patient.

The combination of compounds as discrete units or as a mixed unit can be delivered to the body via a double-ended needle assembly. This would provide a combination drug injection system that, from a user's perspective, would be achieved in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable.

5. Optionally, after the second dose has been computed, the device may be placed in an armed condition. In such an optional armed condition, this may be achieved by pressing and/or holding an "OK" button on a control panel. This condition may provide for greater than a predefined period of time before the device can be used to dispense the combined dose.

6. Then, the user will insert or apply the distal end of the dose dispenser (e.g., a double ended needle assembly) into the desired injection site. The dose of the combination of the primary compound and the secondary compound (and potentially a third medicament) is administered by activating an injection user interface (e.g., an injection button).

Both medicaments may be delivered via one injection needle or dose dispenser and in one injection step. This offers a convenient benefit to the user in terms of reduced user steps compared to administering two separate injections.

The dispense interface can also include a lock out mechanism. Such a lock out mechanism can prevent the dispense interface from being reattached to the drug delivery device once the interface has been initially removed from the device. Such a feature may help reduce the possibility of contamination as well as prevent possible blunting of the dispense interface needle injections ends. These features are described in greater detail below. A lock out mechanism can be implemented via a so called lock out member, which is activated when the cartridge holder is attached to the dispense interface. After removing the dispense interface from the cartridge holder the lock out member prohibits a further use of the dispense interface.

Apart from expiring because of possible dates of expiry, the quality or effectiveness of medicaments may also be affected by influences of the environment, which can not be foretold.

Thus the invention faces the technical problem of further improving the safety and ensuring the quality of medicaments ejected from medical devices in an economic way without the need of additional space in the medical device.

This technical problem is solved by an apparatus, comprising a lock out member configured to be implemented into a medical device, in particular a dispense interface, attachable to a second medical device, in particular a main body, wherein said lock out member is configured to prevent a second attachment of said medical device to said second medical device, wherein said lock out member has at least a first area with a first cross-sectional area, wherein said lock out member has at least a second area having a second cross-sectional area smaller than the first cross-sectional area, such that an electric resistance is defined between opposite ends of the lockout member and wherein said lock out member, at least in the at least one second area, is made of a conductive material.

This way an already implemented part in the medical device can be used for the improvement of the safety and the possible assurance of the quality of medicaments ejected from medical devices. For example, by measuring the resistance between the opposite ends of the lockout member, the temperature can be determined on the basis of the measured resistance. This way, it is possible to get information about the temperature by measuring the resistance of the lock out member. To be able to measure a significant difference in the resistance of the lock out member, it is necessary, that the resistance changes measurably while the temperature goes below or above a safe temperature interval for a medicament. Such a safe temperature interval may be from 0 to 25° C.

By measuring the resistance, it is also possible to identify the lock out member. For example, it may be determined whether a correct lock out member, which can be situated in a dispense interface, is connected by determining whether the resistance of the lockout member is within a certain range of values.

The measuring of the resistance can be performed in various ways. A direct or an alternating current can be used for this. The resistance can be measured in a direct method, for example. But it is as well possible to measure the resistance with an indirect method. As an indirect method one can use an RC-Oscillator, whereas the resistance between the opposite ends of the lockout member provides the at least a part of the resistance for the RC oscillator. The direct measurement of the resistance can be replaced by the measurement of a frequency of the RC oscillator.

By determining the temperature from the resistance between the opposite ends of the lockout member at lest a part of the lockout member can this way be used as a resistance thermometer. A resistance thermometer is understood as any sort of substantially conductive material, the resistance of which changes significantly enough with temperature to be measured.

The first areas are preferably the whole lock out member without the at least one second area. All the first areas have preferably a larger cross-sectional area than the second areas. By providing at least a second area having a reduced cross-sectional area, the influence of this area is dominating the overall resistance of the lock out member. The reduced cross section must be that small, that a resistance change can be measured in the relevant temperature ranges. Preferably there are two second areas with a smaller cross-sectional area compared to the at least one first area. These two second areas might be shaped identically.

Here a lock out member is understood as any member, which is able to prevent a second use of a medical device, in which the lock out member is implemented, after the medical device, such as a dispense interface, is detached from a second device, such as a main body for example. A lock out member can in particular be a lock out spring. This can be any type of elastic object, which can store mechanical energy. Such springs can be design as coils spring, flat springs, cantilever springs or springs with an even more complex design.

In a preferred embodiment the apparatus further comprises means configured to be conductively attached to a device, capable of measuring the resistance of at least said second area of said lock out member. Such means could be any kind of connection interface comprising a conductive material, like simple projections, which conductively attach to a connected main body. The main body may comprise a micro-processor control unit, which can then measure the resistance of the lock out member by well know means in the state of the art. A conductive connection, for example by wires, between the lock out member and the micro-processor control unit can be established for this purpose by means well known in the art.

A medical device may further comprise an electronic circuit for measuring the resistance of the lock out member, for example by contacts that contact the lockout member.

It is further preferred, when said second cross section is at most 30%, in particular at most 20%, preferably at most 10%, of said first cross section. This way a resistance thermometer can be easily provided by a significant reduction in the second area of the lock out member. Surprisingly the functionality of the lock out mechanism is not negatively influenced by the reduction of the cross-sectional area of the second area.

The reduction of the surface can be easily provided by cut outs of the lock out member. This might be one large cut out, or preferably multiple small cut outs in form of holes. Those cut outs are preferably provided in the area of substantially stress-free or non-bent parts of the lock out member. This way the stability of the lock out member is not significantly reduced.

In a preferred embodiment the lock out member is substantially made of metal. This way the functionality of the spring is easily provided and at the same time the first and second areas are conductive and a resistance measurement can be easily performed. Moreover the equalisation of the temperatures of the second areas and the medicaments can be improved.

Not only the resistance measurement of the second areas can be done by a micro-processor control unit, which can then measure the resistance of the lock out member by well know means in the state of the art. But also the determination of a temperature value according to the measured resistance can be done by the micro-processor control unit implemented in the main body of the medical device. This way no further devices for the measurement are needed.

The conductive material of the at least one second area can either comprise a Negative Temperature Coefficient Thermistor or a Positive Temperature Coefficient Thermistor. The resistance of a Negative Temperature Coefficient Thermistor decreases with increasing temperature, while the resistance of a Positive Temperature Coefficient Thermistor increases with increasing temperature. Such thermistors use for example semi-conductive metal oxides or silicon. This way a temperature range of about −100 to over 100° C. can easily be measureable by the resistance measurement. The dependence of the resistance is stronger than that of standard metals.

According to another embodiment said lock out member is configured to be implemented into said medical device by form fit, force fit and/or material bonding. This may be realised by snap locks, threads, glue or similar connection arrangements.

By implementing said lock out member into a housing made of a nonconductive material, such as plastic, it can be easily guaranteed to measure the resistance of the lock out member only, without influencing the resistance measurement by further resistances in contact with the lock out member.

It is further preferred, when said lock out member is configured to be implemented close to at least one cartridge containing a liquid of said medical device. Since the temperature of the liquid is actually of interest, a reasonable value of the temperature of the liquid can be easily determined by positioning the lock out member close to the liquid or to the cartridges containing the liquid respectively.

In a further embodiment said lock out member is configured to be implemented in contact with at least one cartridge containing a liquid of said medical device. By designing and positioning the lock out member in such a way that at least one cartridge can be in contact with the lock out member, while the main body containing the cartridge is attached to the medical device containing the lock out member, a further improvement of the estimation of the actual temperature of the liquid can be made.

Preferably said lock out member is configured to be implemented into a dispense interface. No modifications of the main body, for example, need to be done. The dispense interface provides an easy solution to use its lock out member to measure the temperature. It is possible to design the medical device in such a way, that the dispense interface must be attached to the main body in order to use the medical device. This way it can be assured to be able to measure the temperature, when the medical device is about to be used.

The technical problem is further solved by a method comprising the steps of measuring the electric resistance of at least a second area of a lock out member, wherein said lock out member has at least a first area with a first cross-sectional area, wherein said second area has a second cross-sectional area smaller than the first cross-sectional area and wherein said lock out member, at least in the second area, is made of a conductive material and determining said electric resistance of at least said second area of said lock out member.

This way an easy to implement method is provided, without the use of any additional devices, such as thermometers, and nevertheless being able to for example measure the temperature or detect the type of the lockout member, thus improving the assurance that the temperature did not go below or above a temperature interval, which would deteriorate the quality of medicaments, or that the correct devices (for example dispense interface with lockout member and medical device) are attached.

According to a further embodiment of the method a temperature is determined based at least in part on the determined resistance. By determining the temperature, the assurance that the temperature did not go below or above a temperature interval is improved, which would otherwise deteriorate the quality of medicaments.

According to a further embodiment of the method the resistance is measured at predefined points in times. This way, a power consuming resistance measurement does not need to be done constantly. Those predefined points in time to perform a resistance and thus a temperature measurement, might be saved in the micro-processor control unit or might also be editable by a user.

Preferably the resistance is measured using a direct or indirect method. Direct or alternating current can be used for this. A sufficient and easy measurement of the resistance can be performed by using a direct current provided by an internal battery, for example. The resistance can be measured in a direct method known from the state of the art, for example. But it is as well possible to measure the resistance with an indirect method. As an indirect method one can use an RC-Oscillator, whereas the resistance between the opposite ends of the lockout member provides the at least a part of the resistance for the RC oscillator. The direct measurement of the resistance can be replaced by the measurement of a frequency of the RC oscillator.

In a further embodiment of the method the resistance is measured before a medical device, to which the lock out member is attached, is used. A resistance and thus temperature measurement only need to be done, when the medical device is actually used. The power consumption can this way be further reduced. In case the temperature is outside of a predefined temperature interval, the user can be informed, for example.

The user can further be informed or the use of said medical device can be prohibited, if the measured temperature is and/or was outside of a predefined temperature interval. By doing so, the safety can be further improved. In case the temperature was once outside a predefined allowed temperature interval, the use of the medical device and thus the ejection of a medicament can be completely prevented, for example.

If the determined resistance is used to identify the lock out member, the assurance that the correct devices are attached to each other can be improved. The lock out member can be implemented in a dispense interface, for example, and before it can be used by a user, it can be checked whether the dispense interface is compatible with or allowed to be used with the medical device, to which the dispense interface is attached.

BRIEF DESCRIPTION OF THE FIGURES

These as well as other advantages of various aspects of the present invention will become apparent to those of ordinary skill in the art by reading the following detailed description, with appropriate reference to the accompanying drawings, in which:

FIG. 1 illustrates a perspective view of the delivery device illustrated in FIG. 1a and 1b with an end cap of the device removed;

FIG. 2 illustrates a perspective view of the delivery device distal end showing the cartridge;

FIG. 3 illustrates a perspective view of the cartridge holder illustrated in FIG. 1 with one cartridge retainer in an open position;

DETAILED DESCRIPTION

Figure 4:
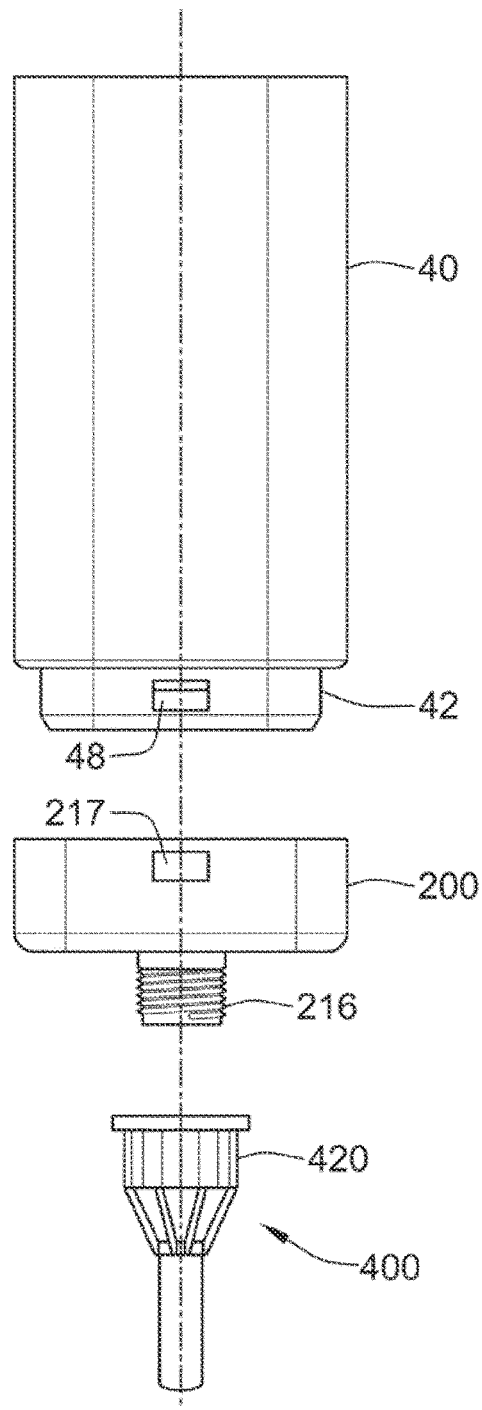
FIG. 4 illustrates a dispense interface and a dose dispenser that may be removably mounted on a distal end of the delivery device illustrated in FIG. 1.

The drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 1).

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 212 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user certain device information, preferably information relating to the medicaments contained within the cartridge holder 40. For example, the user is provided with certain information relating to both the primary medicament (Drug A) and the secondary medicament (Drug B).

As shown in FIG. 3, the first and a second cartridge retainers 50, 52 comprise hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

As mentioned above when discussing FIG. 1, a dispense interface 200 is coupled to the distal end of the cartridge holder 40. FIG. 4 illustrates a flat view of the dispense interface 200 unconnected to the distal end of the cartridge holder 40. A dose dispenser or needle assembly that may be used with the interface 200 is also illustrated and is provided in a protective outer cap 420.

Figure 5:
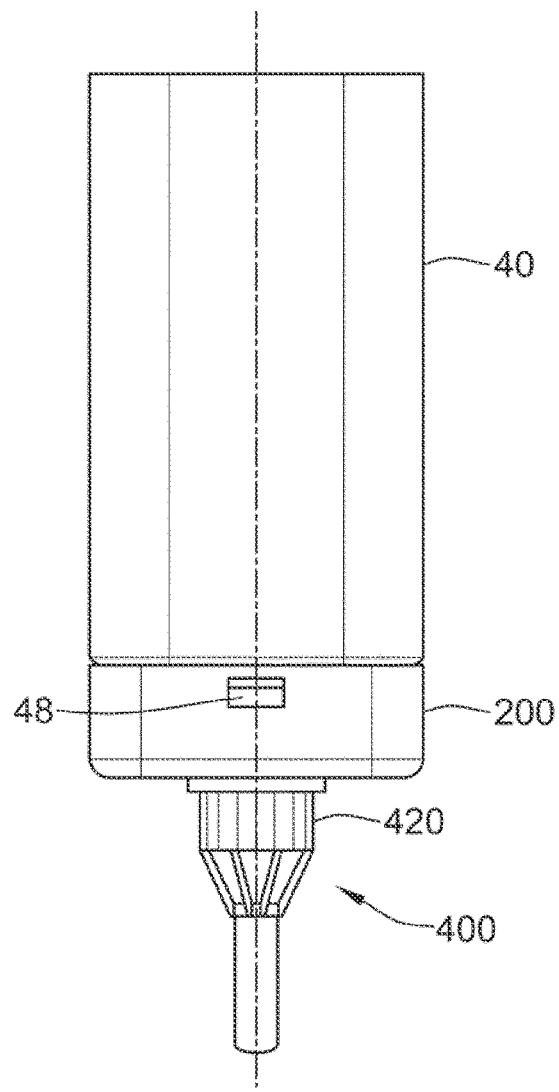
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. The axial attachment means between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
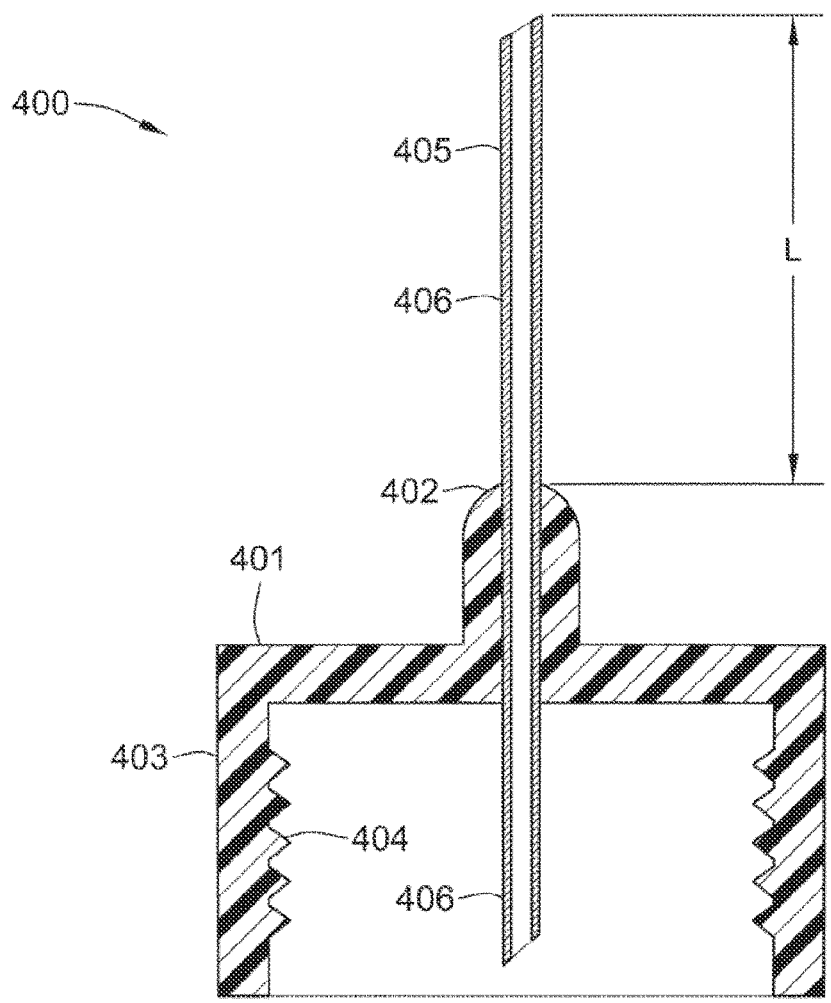
FIG. 6 illustrates one arrangement of the dose dispenser that may be mounted on a distal end of the delivery device.
Figure 7:
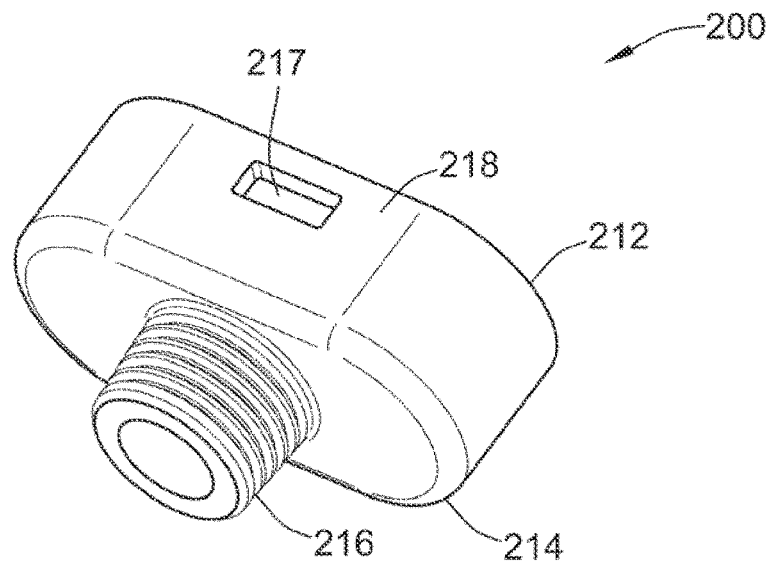
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 402 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Figure 11:
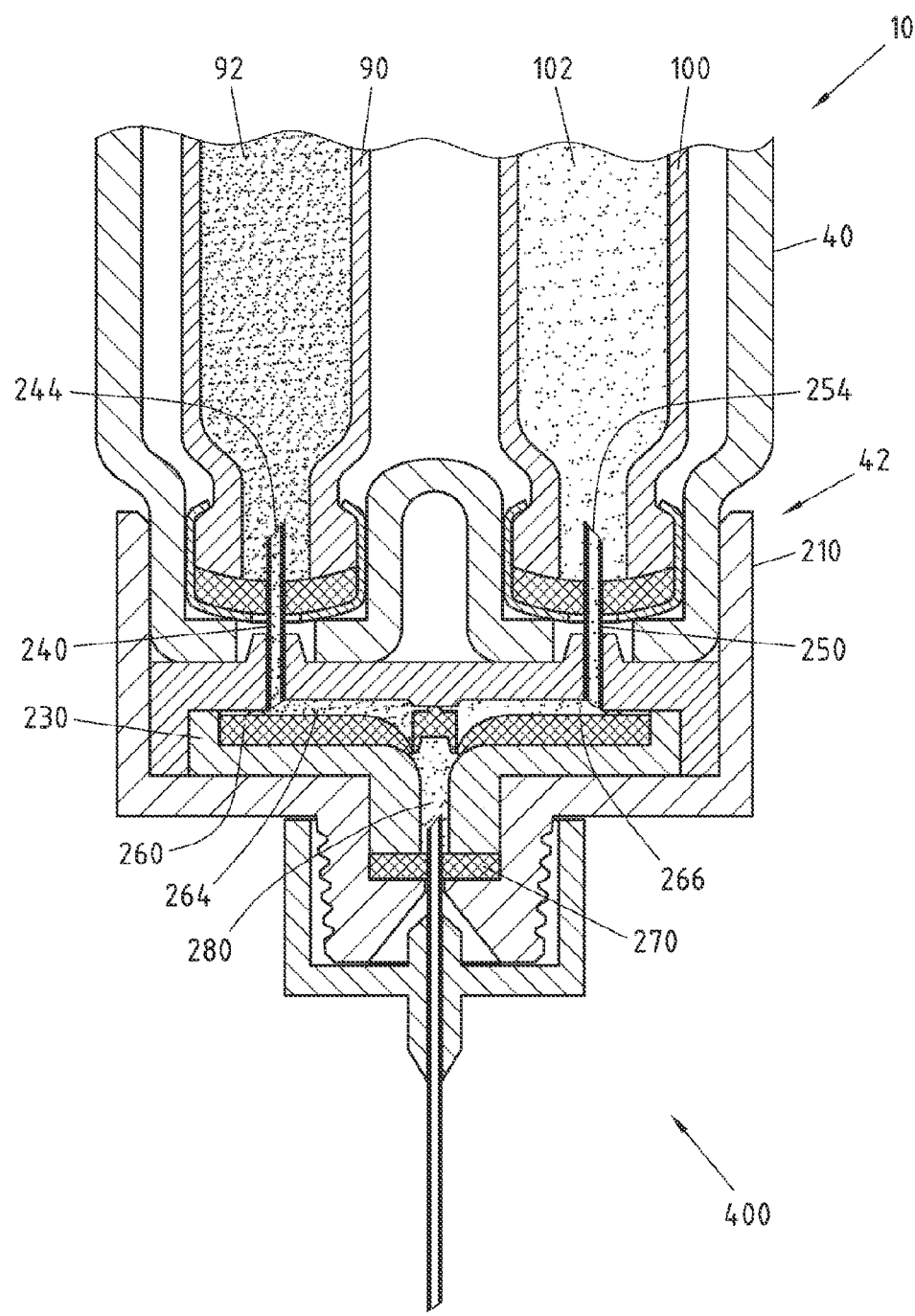
FIG. 11 illustrates a cross-sectional view of the dispense interface and dose dispenser mounted onto a drug delivery device, such as the device illustrated in FIG. 1.
Figure 12:
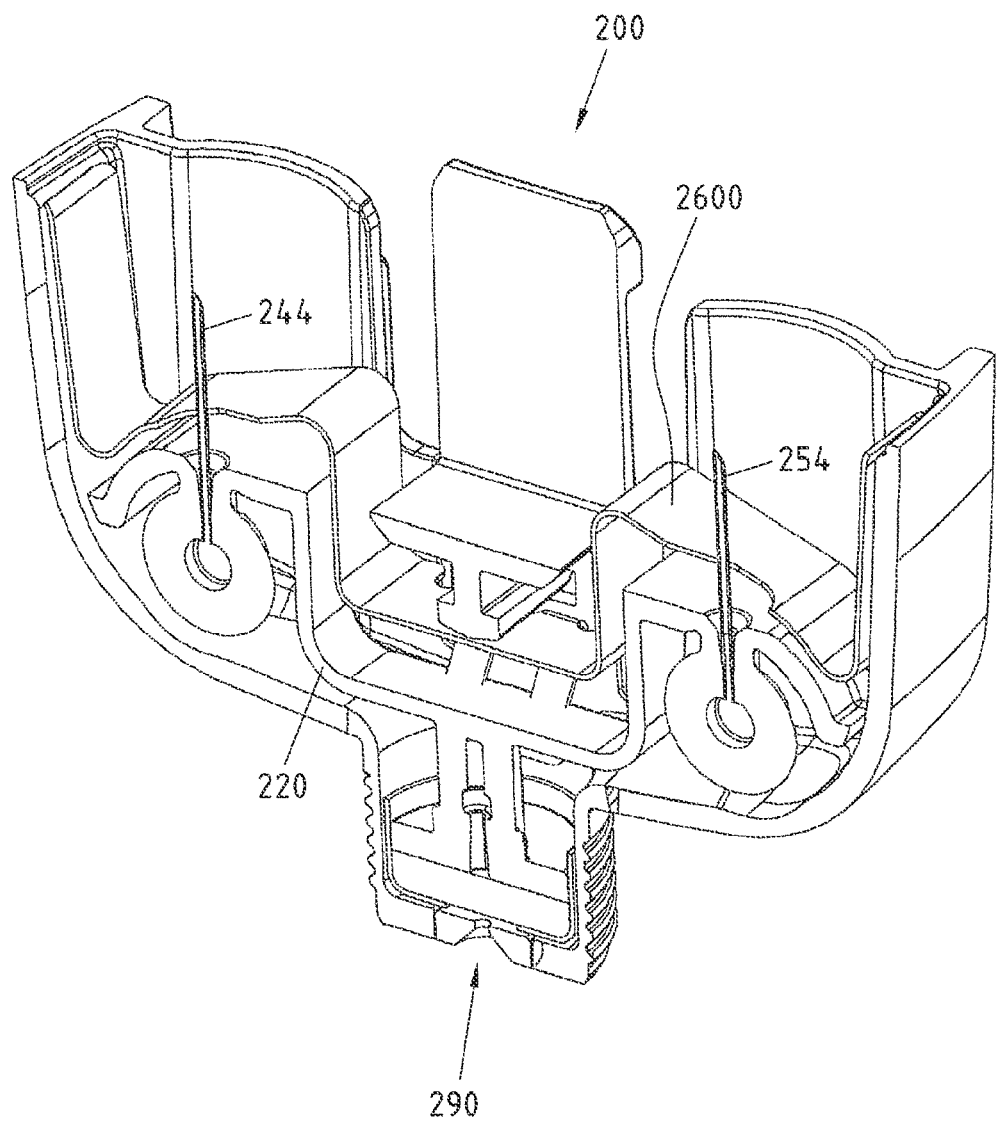
FIG. 12 illustrates a cross sectional view of another dispense interface with a lock out member.

Similarly, a second or proximal piercing end 406 of the needle assembly 400 protrudes from an opposite side of the circular disc so that it is concentrically surrounded by the sleeve 403. In one needle assembly arrangement, the second or proximal piercing end 406 may be shorter than the sleeve 403 so that this sleeve to some extent protects the pointed end of the back sleeve. The needle cover cap 420 illustrated in FIGS. 11 and 12 provides a form fit around the outer surface 403 of the hub 401.

Referring now to FIG. 4-11, one preferred arrangement of this interface 200 will now be discussed. In this one preferred arrangement, this interface 200 comprises:

a. a main outer body 210,
b. an first inner body 220,
c. a second inner body 230,
d. a first piercing needle 240,
e. a second piercing needle 250,
f. a valve seal 260, and
g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213a and a second rib 213b. This first rib 213a is also illustrated in FIG. 10. These ribs 213a and 213b are positioned along the inner surface 215 of the wall 218 of the outer body 210 and create a form fit or snap lock engagement with cooperating grooves 224a and 224b of the first inner body 220. In a preferred arrangement, these cooperating grooves 224a and 224b are provided along an outer surface 222 of the first inner body 220.

Figure 8:
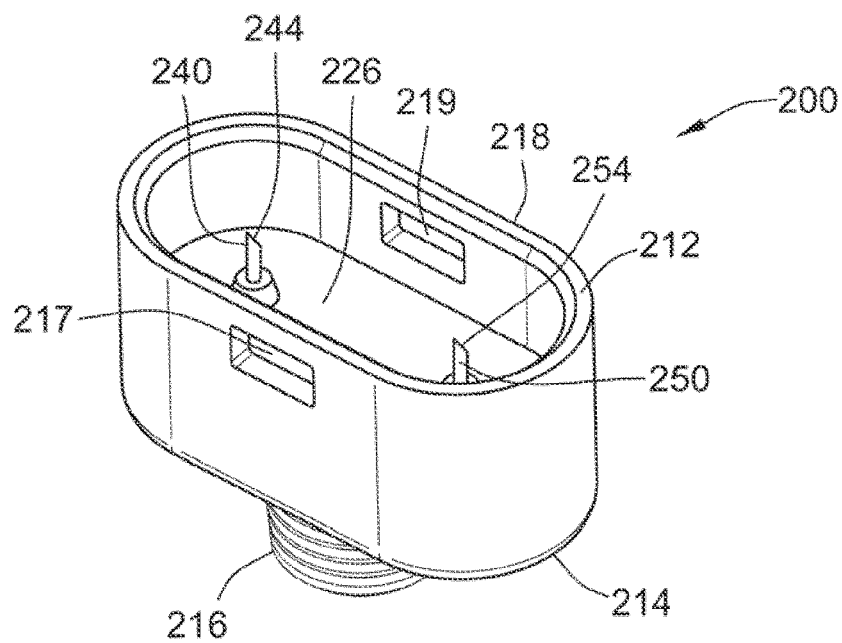
FIG. 8 illustrates another perspective view of the dispense interface illustrated in FIG. 4.
Figure 9:
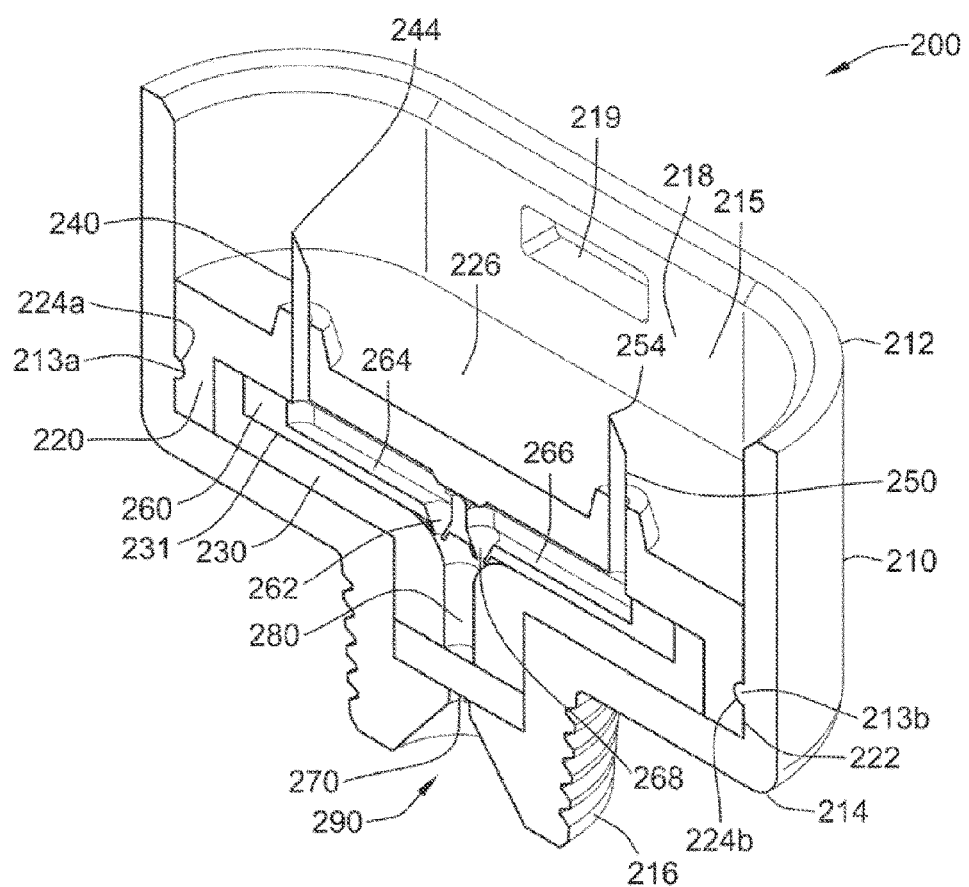
FIG. 9 illustrates a cross-sectional view of the dispense interface illustrated in FIG. 4.
Figure 10:
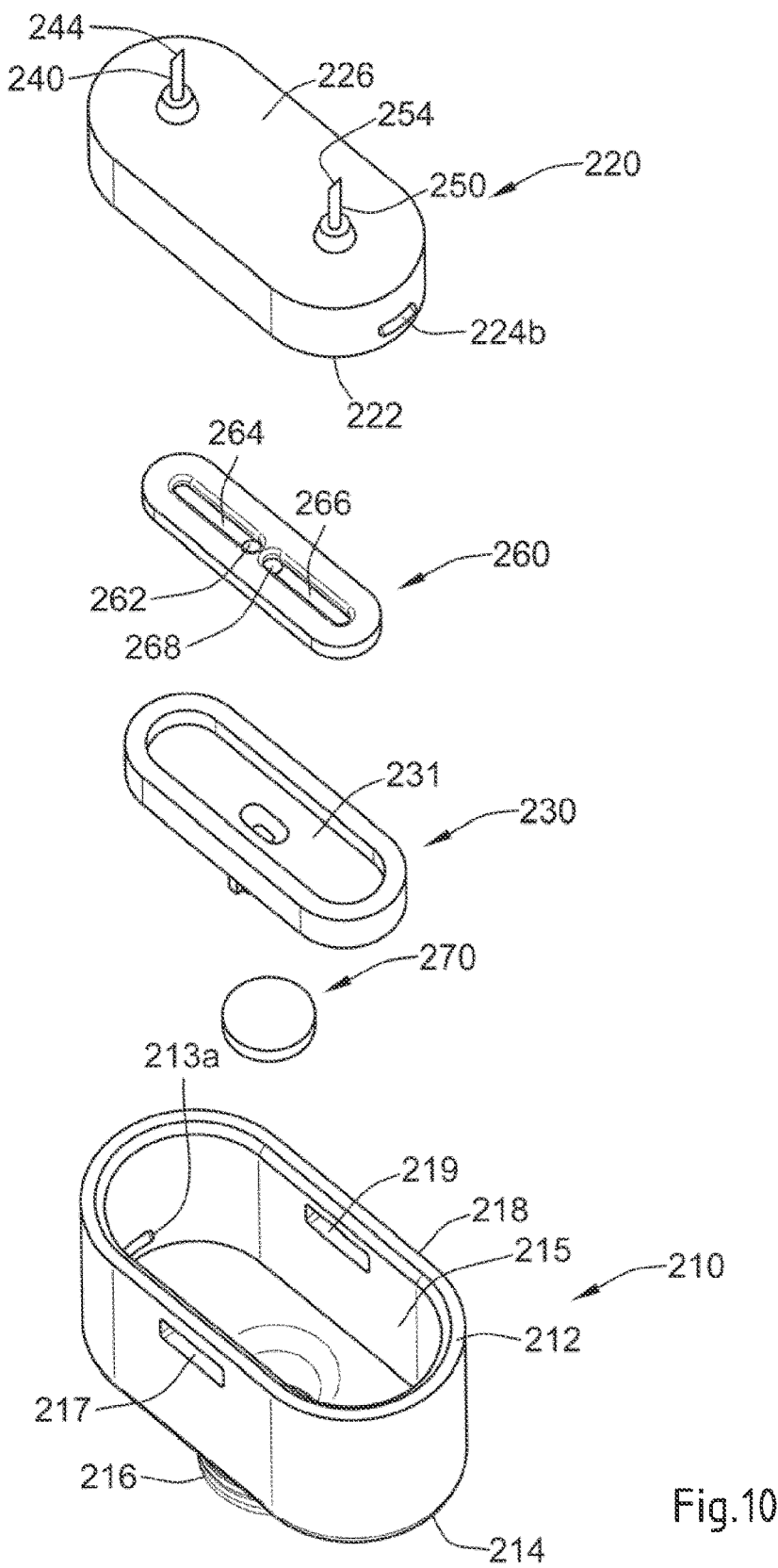
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, the seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

FIG. 11 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

Figure 13:
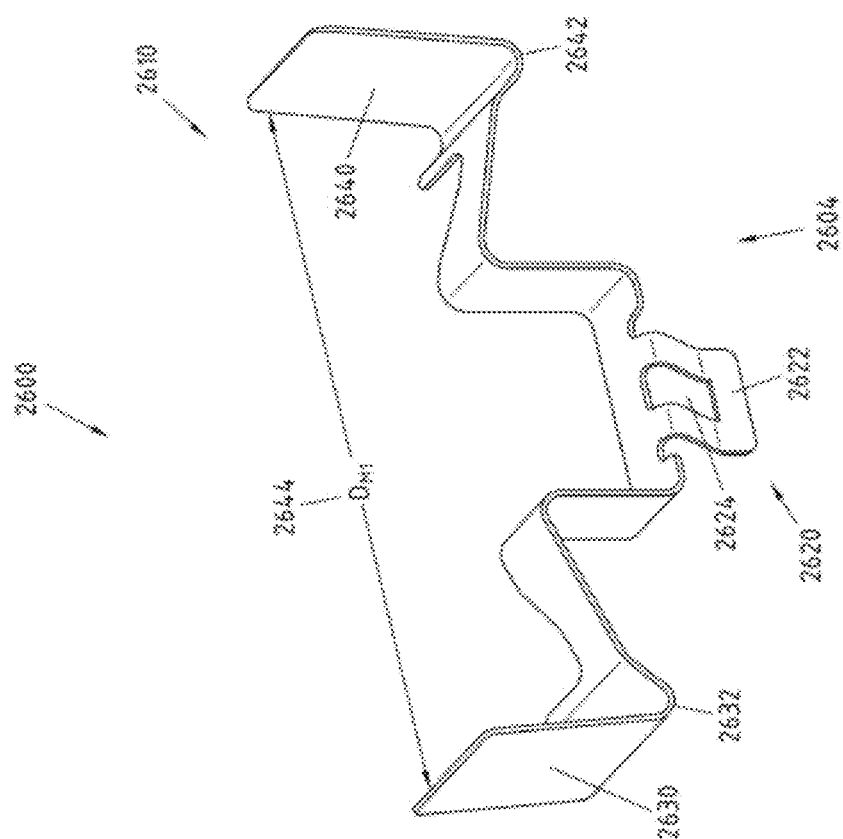
FIG. 13 illustrates a perspective view of a lock out member of the dispense interface illustrated in FIG. 12.

FIG. 12 illustrates a cross sectional view of another dispense interface with a lock out member. As may be seen from FIG. 12, the dispense interface 200 further comprises a dispense interface lockout member in the form of a lockout spring 2600. FIG. 13 illustrates a perspective view of such one arrangement of such a lock out member 2600 in an initial, unbiased or unstressed state. One reason that a lock out member may be incorporated into a dispense interface, such as the interface 200 illustrated in FIG. 12, is to ensure that once the dispense interface is removed from the drug delivery device, the dispense interface cannot be re-attached and used a second time. Preventing re-attachment tends to ensure that medicament is not allowed to reside in the dispense interface 200 indefinitely and contaminate the drug delivered to the patient.

FIG. 12 illustrates a perspective cross sectional view of one arrangement of the dispense interface lock out member 2600 illustrated in FIG. 13 seated on the inner body 220 illustrated in FIG. 12. In this illustrated arrangement, the lock out member resides in a first or an initial position. As illustrated, the lock out member 2600 extends from a distal spring end 2604 to a proximal spring end 2610. Near its distal end 2604, the lock out member 2600 comprises a spring tip 2620. This spring tip 2620 comprises a tab 2622 defining a recess 2624.

Near its proximal end 2610, the lock out member 2600 comprises a first spring arm 2630 and a second spring arm 2640. For example, the first spring arm 2630 extends proximally from a first pivot point 2632 of the spring 2600. Similarly, the second spring arm 2640 extends proximally from a second pivot point 2642 of the spring 2600. In the initial spring position illustrated in FIG. 13 and FIG. 12, both the first and the second spring arms 2630, 2640 reside in an unstressed state. That is, both arms flex radially outward, away from one another a spaced amount defining an initial distance DM1 2644 of a mouth created between the first and the second spring arm 2630, 2640. When the spring 2600 is placed within a stressed state (so as to lock out the spring preventing re-attachment), the first and second spring arms 2630, 2640 flex towards one another at the first and second pivot points 2632, 2642, respectively. This flexing causes the arms 2630, 2640 to reduce the initial distance DM1 of the mouth to a smaller second mouth distance DM2.

Figure 14:
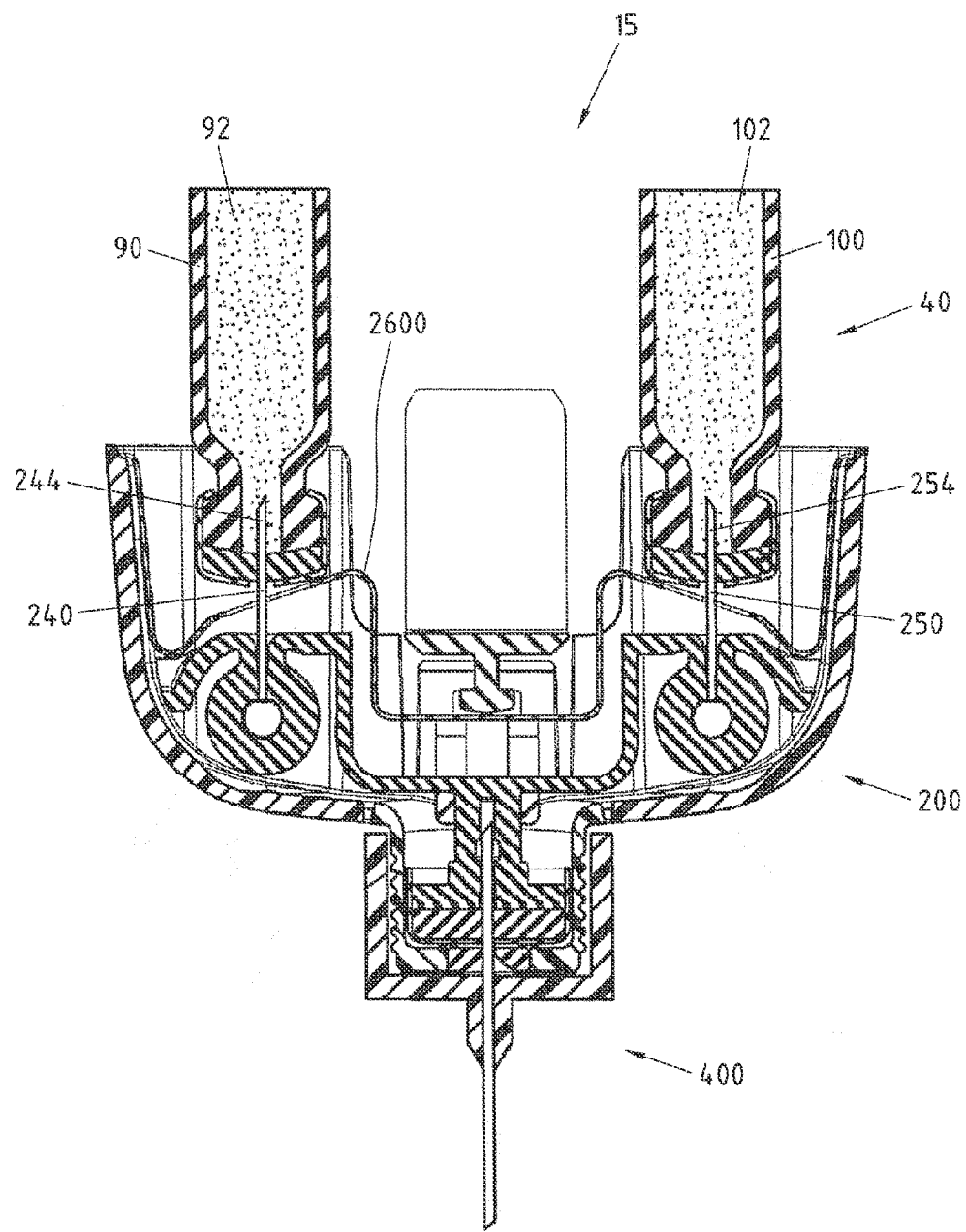
FIG. 14 illustrates a cross-sectional view of the dispense interface of FIG. 12 mounted on a drug delivery device along with a dose dispenser attached to the dispense interface.

FIG. 14 illustrates the dispense interface 200 after it has been mounted onto the distal end 15 of the cartridge holder 40 of the drug delivery device 10. As illustrated, a double ended needle assembly 400 is also mounted to the distal end of this interface. The cartridge holder 40 is illustrated as having a first cartridge 90 containing a first medicament 92 and a second cartridge 100 containing a second medicament 102. As can be seen the lock out member 2600 is in direct contact with the cartridges 90, 100, allowing for a better equalisation between the temperature of the medicaments 102, 92 and the lock out member 2600.

Figure 15A:
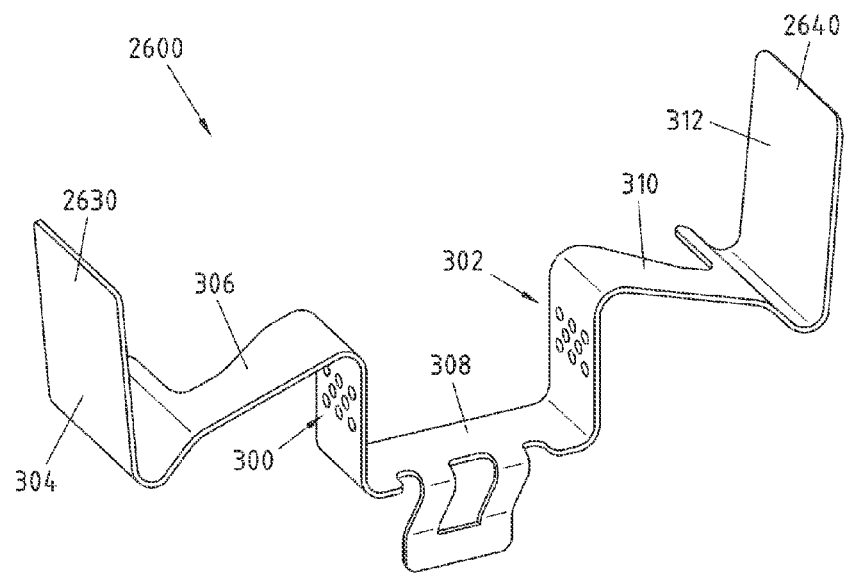
FIG. 15a illustrates a perspective view of a an embodiment of a lock out member according to the invention
Figure 15B:
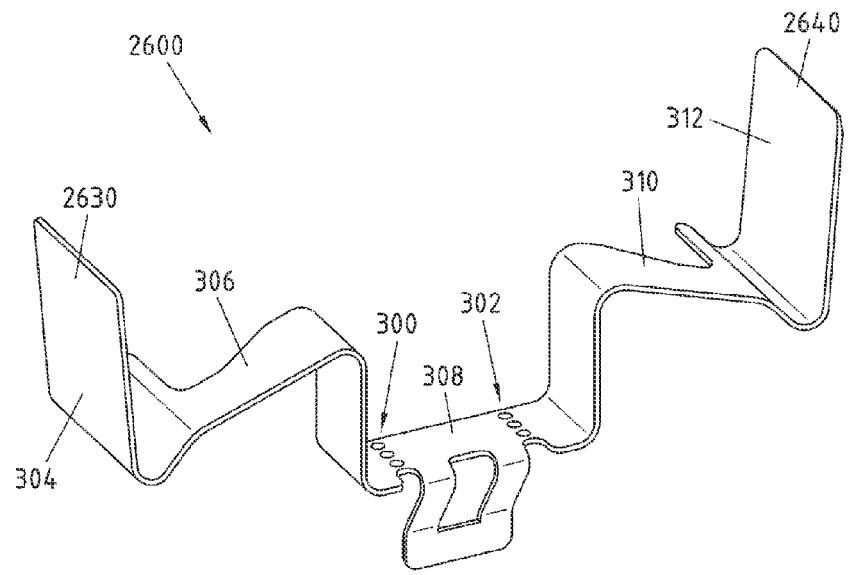
FIG. 15b illustrates a perspective view of a further embodiment of a lock out member according to the invention

FIGS. 15a and 15b show a modification of the lock out member 2600 illustrated in FIG. 13. The modifications, which have been done, compared to the lock out member 2600 illustrated in FIG. 13 are the cut outs in the second areas 300 and 302. By perforating the lock out member 2600 with holes the cross-sectional area of the second areas 300 and 302 is reduced, so that the electric resistance between opposite ends of the lockout member may be defined at a certain value or level, for example between the spring arms 2630 and 2640. In an example embodiment, the lock out member 2600 may be used as a resistance thermometer. The resistance measurement can easily be realised, if the lock out member is made of metal and by using the spring arms 2630 and 2640 as two contacts for a resistance measurement. The current has to pass the areas 300 and 302, which have a high resistance compared to the first areas 304, 306, 308, 310 and 312. The second areas 300, 302 therefore dominate the resistance measurement and can be used as a resistor with a predefined resistance, or as a resistance thermometer. By implementing the perforations in a substantially plane part of the lock out member 2600 the stability of the lock out member 2600 is not significantly influenced. Different dispense interfaces 20 may comprise lock out members 2600 with different resistance values.

The drug delivery device may comprise an electronic circuit for measuring the resistance of the lock out member 2600, for example by contacts that contact the spring arms 2630 and 2640 when the dispense interface 200 is attached to the device 10. By measuring the resistance, the lock out member 2600 may be identified. For example, it may be determined whether a correct lock out member and/or dispense interface is connected by determining whether the resistance of the lockout member 2600 is within a certain range of values.

By providing two second areas 300, 302 the resistance of these areas is measured in series in this case. Since the temperature at the two second areas are very likely the same, this one temperature can still be determined easily by one skilled in the art. By providing two second areas 300, 302 the effect of the temperature on the resistance can be increased in a simple way. By providing the second areas 300, 302 symmetrically in the lock out member 2600, the lock out member 2600 is still stressed uniformly and symmetrically, even with the cut outs.

Of course, different numbers of cut outs in a second area and different numbers of second areas may be provided in a lock out member.

Figure 15C:
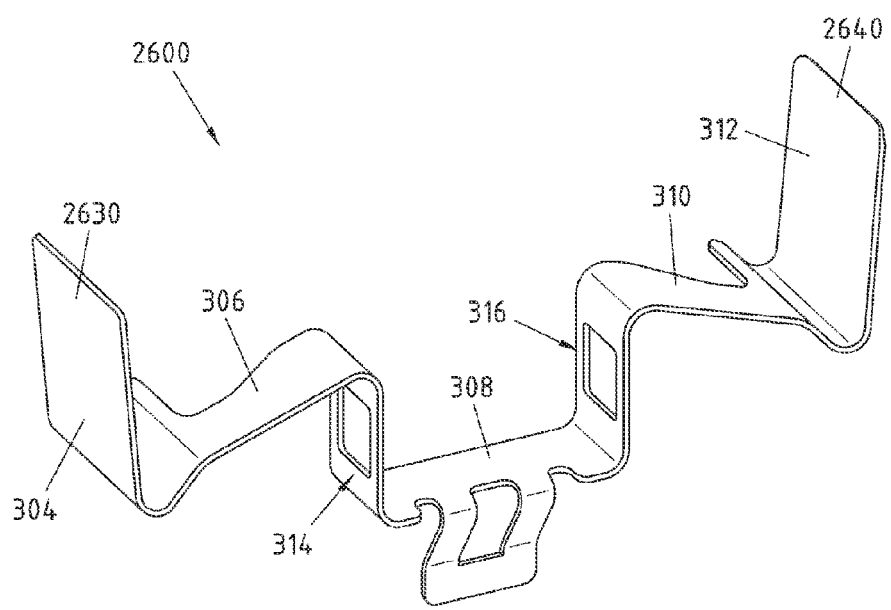
FIG. 15c illustrates a perspective view of a further embodiment of a lock out member according to the invention

FIG. 15c shows another embodiment of the second areas 310, 312 in the lock out member 2600. The reduction of the cross section of the second areas 314, 316 is in this case achieved by two large cut outs, which are easier to produce than multiple smaller cut outs.

Such cut outs might be produced by first manufacturing the lock out member 2600 as illustrated in FIG. 13 and afterwards laser processing the second areas 300, 302, 314, 316 and thus producing the cut outs. The cut outs might also be produced with mechanical tools, by stamping or punching, for example. Though, the second areas might also be incorporated into the lock out member 2600 during the manufacture of the lock out member itself The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly- Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39), des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Trp(O2)25, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. An apparatus, comprising:
a lock out spring configured to be implemented into a medical device, in particular a dispense interface, attachable to a second medical device, in particular a main body,
wherein said lock out spring comprises a first spring arm and a second spring arm and is configured to prevent a second attachment of said medical device to said second medical device by the first spring arm and the second spring arm flexing inwardly towards one another at a first and second pivot points of the lock out spring,
wherein said lock out spring has a first end, a second end, and at least a first area with a first cross-sectional area between said first end and said second end through which an electric current is configured to flow, and
wherein said lock out spring has at least a second area between said first end and said second end having a second cross-sectional area smaller than the first cross-sectional area through which said electric current is configured to flow,
such that an electric resistance is defined between said first end and said second end of the lock out spring, and
wherein said lock out spring, at least in the at least one second area and at least one first area, is made of a conductive material,
wherein the apparatus is configured to measure the resistance between the first and second end of the lockout spring, to determine a temperature using the measured resistance, and to inform a user of the temperature or to prohibit use of the apparatus if the temperature is or was outside of a predefined temperature interval.

2. Apparatus according to claim 1, wherein said apparatus further comprises means configured to be conductively attached to a device, capable of measuring the resistance of at least said second area of said lock out spring.

3. Apparatus according to claim 1, wherein said second cross section is at most 30%, in particular 20%, preferably 10%, of said first cross section.

4. Apparatus according to claim 1, wherein said lock out spring is substantially made of metal.

5. Apparatus according to claim 1, wherein said conductive material comprises a Negative Temperature Coefficient Thermistor or a Positive Temperature Coefficient Thermistor.

6. Apparatus according to claim 1, wherein said lock out spring is configured to be implemented into said medical device by form fit, force fit and/or material bonding.

7. Apparatus according to claim 1, wherein said lock out spring is configured to be implemented close to at least one cartridge containing a liquid of said medical device.

8. Apparatus according to claim 1, wherein said lock out spring is configured to be implemented in contact with at least one cartridge containing a liquid of said medical device.

9. Apparatus according to claim 1, wherein said lock out spring is configured to be implemented into a dispense interface.

10. A method comprising the steps of:
measuring the electric resistance of the at least one second area of the lock out spring according to claim 1, and
determining the electric resistance of at least said second area of said lock out spring by measuring the electrical resistance between the first and second end, determining a temperature using the measured electrical resistance, and informing a user of the temperature or prohibiting use of the apparatus if the temperature is or was outside of a predefined temperature interval.

11. Method according to claim 10, wherein a temperature is determined based at least in part on the determined resistance.

12. Method according to claim 10, wherein the resistance is measured using a direct or indirect method.

13. Method according to claim 10, wherein the resistance is measured before the medical device, to which the apparatus is attached, is used.

14. Method according to claim 10, wherein a user is informed or the use of said medical device is prohibited, if the measured temperature is and/or was outside of a predefined interval.

15. Method according to claim 10, wherein the determined resistance is used to identify the lock out spring.

\* \* \* \* \*